US012472076B2

(12) United States Patent
Lee et al.

(10) Patent No.: US 12,472,076 B2
(45) Date of Patent: Nov. 18, 2025

(54) OBLIQUE LATERAL INSERTION-TYPE INTERVERTEBRAL CAGE

(71) Applicant: Sang Ho Lee, Seoul (KR)

(72) Inventors: Sang Ho Lee, Seoul (KR); Ju Hee Jang, Daegu (KR)

(73) Assignee: Sang Ho Lee, Seoul (KR)

( * ) Notice: Subject to any disclaimer, the term of this patent is extended or adjusted under 35 U.S.C. 154(b) by 459 days.

(21) Appl. No.: 17/627,322

(22) PCT Filed: Jul. 14, 2020

(86) PCT No.: PCT/KR2020/009252
§ 371 (c)(1),
(2) Date: Feb. 18, 2022

(87) PCT Pub. No.: WO2021/015478
PCT Pub. Date: Jan. 28, 2021

(65) Prior Publication Data

US 2022/0273454 A1 Sep. 1, 2022

(30) Foreign Application Priority Data

Jul. 23, 2019 (KR) ........................ 10-2019-0089107

(51) Int. Cl.
*A61F 2/44* (2006.01)
*A61F 2/30* (2006.01)
*A61F 2/46* (2006.01)

(52) U.S. Cl.
CPC ............ *A61F 2/447* (2013.01); *A61F 2/4611* (2013.01); *A61F 2/4657* (2013.01); *A61F 2002/30593* (2013.01); *A61F 2002/4629* (2013.01)

(58) Field of Classification Search
CPC ...... A61F 2/447; A61F 2/4611; A61F 2/4657; A61F 2002/30593; A61F 2002/4629
See application file for complete search history.

(56) References Cited

U.S. PATENT DOCUMENTS

2009/0062917 A1* 3/2009 Foley .................... A61F 2/4455 623/17.16
2011/0172775 A1* 7/2011 Flickinger ............. A61F 2/4465 623/17.16

(Continued)

FOREIGN PATENT DOCUMENTS

KR 10-2017-0001989 A 1/2017
KR 10-1794485 B1 11/2017

(Continued)

*Primary Examiner* — Nicholas J Plionis
(74) *Attorney, Agent, or Firm* — NKL Law; Jae Youn Kim

(57) ABSTRACT

A cage to be inserted between vertebrae reduces a risk of damage to organs and nerves in the process of insertion surgery and facilitates the process of insertion surgery. The cage can be inserted in one insertion direction between a plurality of vertebrae, wherein the insertion direction forms a predetermined insertion angle with respect to the anterior aspect of the spine, and an upper surface and a lower surface of the cage are provided to correspond to a lower surface and an upper surface of the vertebrae. Also, the cage is stably fixed, and side effects after surgery is reduced. Also, the surgery time is reduced, and a burden on the patient is reduced. In addition, advantages of anterior insertion and direct lateral insertion are combined, and thus post-surgery outcomes in patients may be improved.

9 Claims, 18 Drawing Sheets

(56) References Cited

U.S. PATENT DOCUMENTS

| | | | | |
|---|---|---|---|---|
| 2012/0277866 | A1* | 11/2012 | Kalluri | A61F 2/4611 623/17.16 |
| 2014/0277497 | A1* | 9/2014 | Bennett | A61F 2/4455 623/17.16 |
| 2015/0100129 | A1 | 4/2015 | Waugh et al. | |
| 2016/0045332 | A1 | 2/2016 | Kana et al. | |
| 2016/0081812 | A1* | 3/2016 | Waugh | A61F 2/4684 623/17.16 |
| 2019/0117410 | A1* | 4/2019 | Parry | A61F 2/4455 |

FOREIGN PATENT DOCUMENTS

| | | | |
|---|---|---|---|
| KR | 10-1822632 | B1 | 1/2018 |
| WO | 2019-013558 | A1 | 1/2019 |
| WO | 2019-013559 | A1 | 1/2019 |

* cited by examiner

OBLIQUE LATERAL INSERTION-TYPE INTERVERTEBRAL CAGE

TECHNICAL FIELD

The present invention relates to a cage to be inserted between vertebrae through the oblique lateral aspect, and more particularly, to a cage that is inserted between vertebrae through the oblique lateral aspect, which forms a predetermined insertion angle with respect to the anterior or posterior of the spine, to maintain and support the spacing between the vertebrae.

BACKGROUND ART

As conventional cage insertion methods, anterior lumbar interbody fusion (ALIF), direct lateral interbody fusion (DLIF), and posterior lumbar interbody fusion (PLIF) are performed.

Because organs are located in front of the spine, in order to insert a cage through the anterior aspect, the organs should be temporarily moved laterally, or the cage should be inserted through a portion between the organs. Therefore, because there is a risk of damage to the organs, and the aorta and vena cava, the largest blood vessels of the human body, need to be pulled, there is a problem in that surgery is very difficult and dangerous and thus a skilled specialist is required. In addition, because nerves are located in the back of the spine, and the vertebral arches and vertebral processes are located on a cage insertion path, in a case where the cage is inserted through the posterior aspect, there is a risk of damage to muscles and nerves, and there is a problem in that a vertebra should be removed.

Also, the psoas muscles are located on the sides of the spine, and nerves going to the legs are entangled in the psoas muscles and pass through the psoas muscles. Therefore, in a case where the cage is inserted through the direct lateral aspect, in order to perform surgery, the psoas muscles should be split on both sides to expose a vertebral body space, and in this process, there is a possibility of causing muscle damage and damage to the nerves going to the legs.

In order to address the above problems, surgery in which a cage is inserted through the oblique lateral aspect may be performed. However, because the conventional cage has a structure corresponding to the anterior, direct lateral, or posterior aspect, the cage should be rotated after being inserted through the oblique lateral aspect, and thus there is a difficulty in the surgery.

RELATED ART DOCUMENT

Patent Document

Korean Patent Registration No. 10-1822632 (Date of Registration: Jan. 22, 2018)

Korean Patent Registration No. 10-1794485 (Date of Registration: Oct. 31, 2017)

DISCLOSURE

Technical Problem

The present invention is directed to providing an oblique lateral insertion type cage that reflects advantages of anterior insertion and direct lateral insertion.

The present invention is also directed to providing a cage with a reduced risk of damage to organs, muscles, and nerves in the process of insertion surgery.

The present invention is also directed to providing a cage which is easy to insert in the process of insertion surgery.

The present invention is also directed to providing a cage which is correctly placed between vertebrae when inserted through the oblique lateral aspect.

Technical Solution

One aspect of the present invention provides a cage inserted between a plurality of vertebrae, wherein the cage is supported while being inserted in one insertion direction to form a predetermined insertion angle with respect to the anterior aspect of the spine and being correctly placed between the vertebrae.

Advantageous Effects

According to the present invention, a risk of damage to organs, muscles, and nerves is reduced in the process of cage insertion surgery.

Also, according to the present invention, the process of cage insertion surgery is facilitated.

Also, according to the present invention, the cage can be stably fixed, and thus side effects after surgery can be reduced.

Also, according to the present invention, the surgery time is reduced, and thus a burden on the patient is reduced.

In addition, according to the present invention, advantages of anterior insertion and posterior insertion are combined, and thus post-surgery outcomes in patients can be improved.

MODES OF THE INVENTION

Terms used herein will be briefly described, and embodiments of the present invention will be described in detail.

As the terms used herein, general terms that are currently widely used have been selected in consideration of functions in the present invention, but the terms may be changed according to the intention or practice of those of ordinary skill in the art, the advent of new technology, and the like.

MODES OF THE INVENTION

Also, in certain cases, terms may have been arbitrarily selected by the applicant, and in this case, the meaning will be described in detail in the corresponding part of the invention. Therefore, the terms used herein should be defined on the basis of the meanings of the terms and the content throughout the specification, rather than being defined simply on the basis of the names of the terms.

Hereinafter, embodiments according to the present invention will be described in detail with reference to the accompanying drawings.

Figure 1:
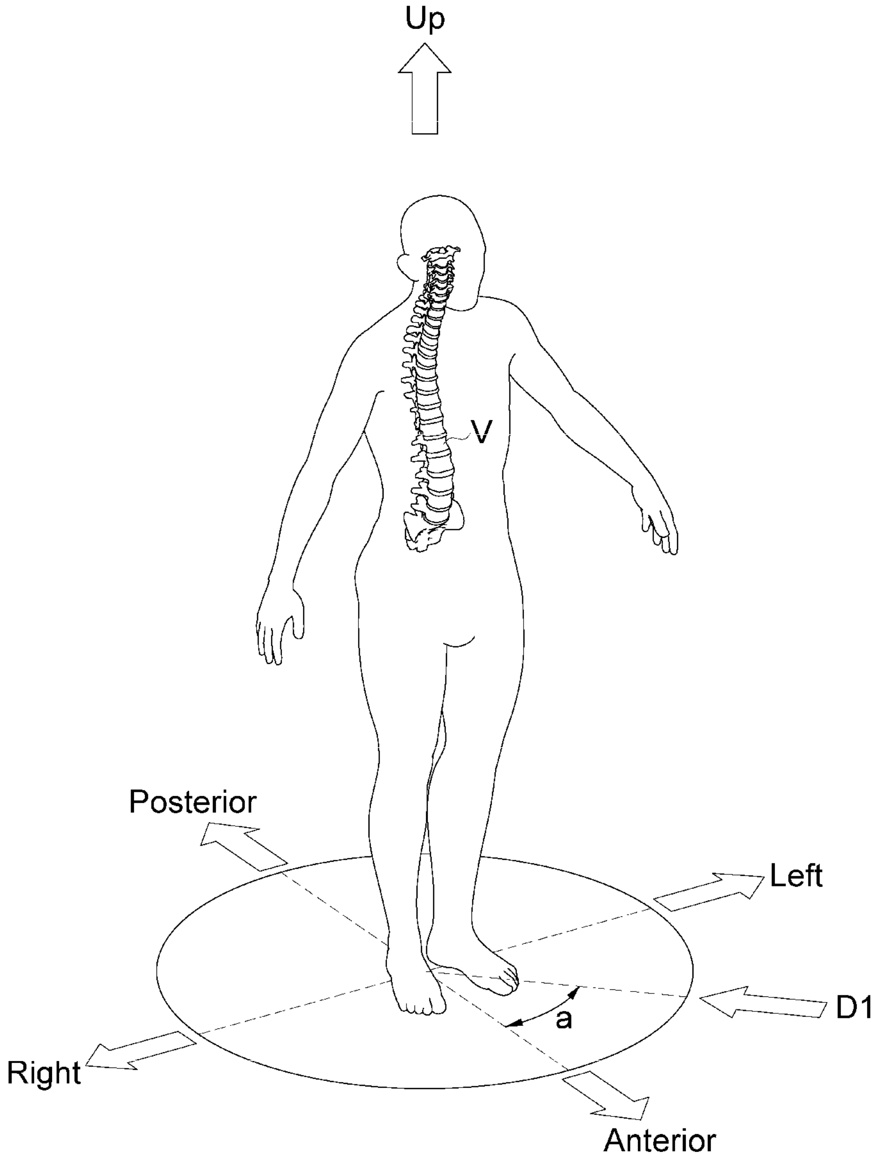
FIG. 1 is a view illustrating the directional relationships used in the description of the present invention.

FIG. 1 is a view illustrating the directional relationships used in the description of the present invention. In the description, "anterior" refers to a direction forward from the spine, and "posterior" refers to a direction rearward from the spine. That is, "anterior" refers to a direction toward the abdomen, and "posterior" refers to a direction toward the back. Also, in the description, "left" refers to a direction toward the left of the spine, and "right" refers to a direction toward the right of the spine. Also, in the description, "up" refers to a direction toward the skull from the spine, and "upper surface" refers to a surface facing upward. Likewise, "down" refers to a direction toward the coccyx from the spine, and "lower surface" refers to a surface facing downward.

Also, in the description, "insertion direction" refers to a direction in which a cage 10 according to the present invention is inserted between vertebrae. The cage 10 according to the present invention is inserted in an insertion direction D1 that forms a predetermined insertion angle a with respect to the anterior aspect of the spine.

Figure 2:
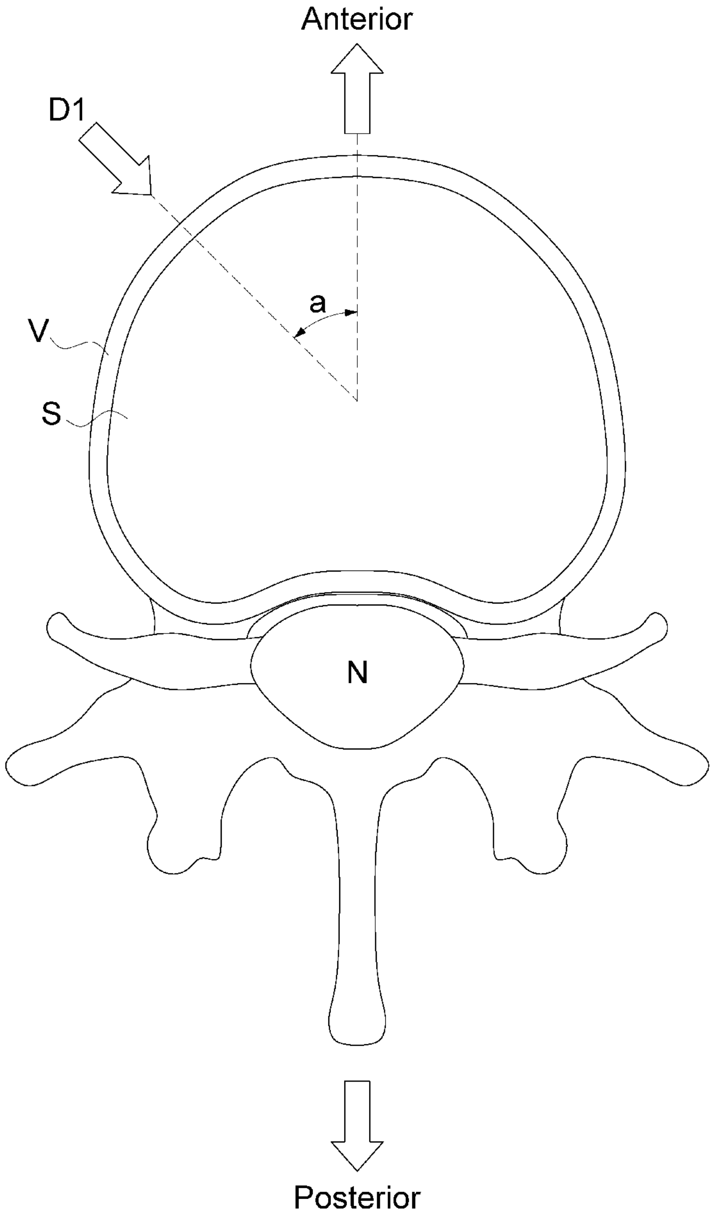
FIG. 2 is a plan view illustrating an insertion direction of a cage according to an embodiment of the present invention.

FIG. 2 is a plan view illustrating the insertion direction D1 of the cage 10 according to an embodiment of the present invention.

Originally, an intervertebral disc is present between vertebrae V. Hereinafter, a space in which a normal intervertebral disc is located will be referred to as a vertebral body space S. A nerve N is located behind the vertebral body space S.

When an abnormality occurs in the intervertebral disc and thus the intervertebral disc is not able to perform its role properly, the cage 10 is inserted to maintain the spacing between the vertebrae and support the vertebrae, in place of a part of the intervertebral disc or the entire intervertebral disc. Hereinafter, an upper vertebra supported by an upper surface of the cage 10 will be referred to as "upper bone." Also, a lower vertebra supported by a lower surface of the cage 10 will be referred to as "lower bone." That is, a lower surface of an upper bone V1 is supported by coming in contact with the upper surface of the cage 10, and an upper surface of a lower bone V2 is supported by coming in contact with the lower surface of the cage 10.

As conventional surgery for inserting the cage 10, anterior lumbar interbody fusion (ALIF), direct lateral interbody fusion (DLIF), and posterior lumbar interbody fusion (PLIF) are performed. However, because organs are located in front of the spine, in order to insert the cage 10 through the anterior aspect, the organs should be temporarily moved laterally, or the cage 10 should be inserted through a portion between the organs. Therefore, because there is a risk of damage to the organs, and the aorta and vena cava, the largest blood vessels of the human body, need to be pulled, there is a problem in that surgery is difficult and dangerous and thus a skilled specialist is required.

In addition, because nerves are located in the back of the spine, and the vertebral arches and vertebral processes are located on an insertion path for the cage 10, even in a case where the cage 10 is inserted through the posterior aspect, there is a risk of damage to muscles and nerves, and there is a problem in that a vertebra should be removed.

Also, the psoas muscles are located on the sides of the spine, and nerves going to the legs are entangled in the psoas muscles and pass through the psoas muscles. Therefore, in a case where the cage is inserted through the direct lateral aspect, in order to perform surgery, the psoas muscles should be split on both sides to expose the vertebral body space S, and in this process, there is a possibility of causing muscle damage and damage to the nerves going to the legs.

In order to address the above problems, the present invention provides the cage 10 that is inserted in the insertion direction D1 which is the oblique lateral aspect forming the predetermined insertion angle a with respect to the anterior or posterior aspect of the spine. In the present embodiment, description will be given on the basis of the case where the insertion direction D1 forms the predetermined insertion angle a with respect to the anterior aspect of the spine. Preferably, the insertion angle a may be in a range of 25° to 65°.

Figure 3:
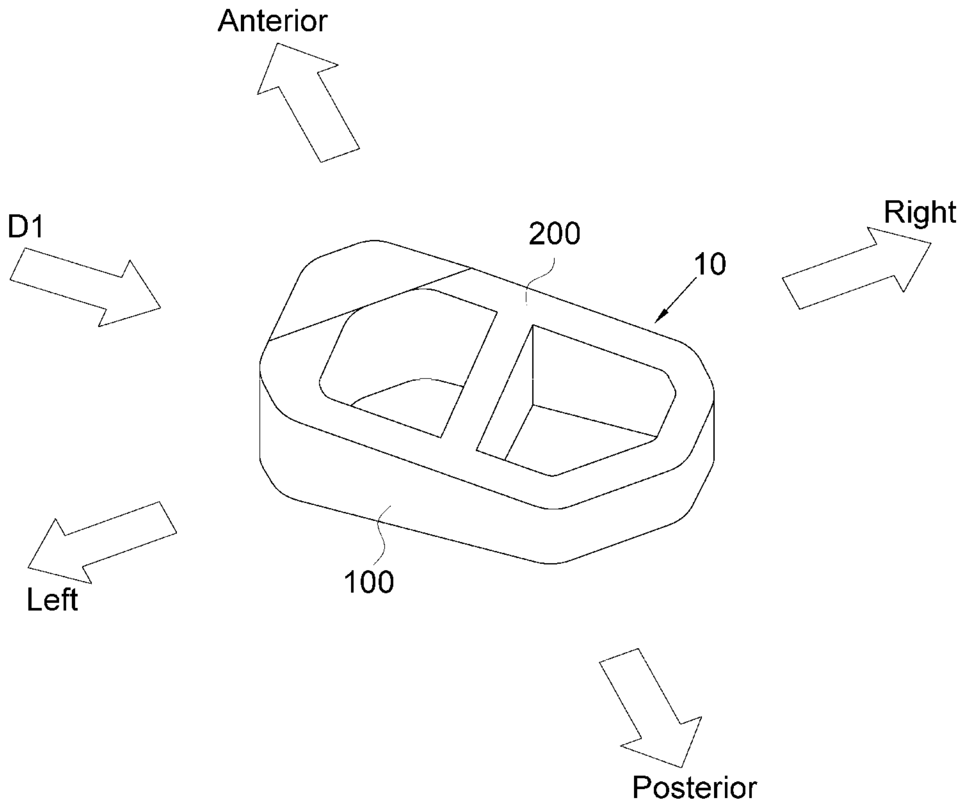
FIG. 3 is a perspective view illustrating a cage according to an embodiment of the present invention.

FIG. 3 is a perspective view illustrating the cage 10 according to an embodiment of the present invention.

According to the present invention, the cage 10 is supported while being inserted in the insertion direction D1 to form the predetermined insertion angle a with respect to the anterior aspect of the spine and being correctly placed between the vertebrae V. Here, "being correctly placed" refers to being suitably placed for the outer shape of the cage 10 to correspond to the vertebral body space S and support the vertebrae. That is, "being correctly placed" refers to being placed so that the outer shape of the cage 10 does not protrude from the vertebral body space S and is supported while suitably coming in contact with the upper bone V1 and the lower bone V2.

The cage 10 according to the present invention includes an outer peripheral surface 100 and an inclined surface 200 so that it is correctly placed while being inserted in the insertion direction D1. Here, the outer peripheral surface 100 is a peripheral surface including the front, rear, left, and right sides of the cage 10. Also, the inclined surface 200 is an inclined surface constituting the upper surface and lower surface of the cage 10.

Hereinafter, the outer peripheral surface 100 according to an embodiment of the present invention will be described in detail with reference to FIGS. 4 to 7.

Figure 4:
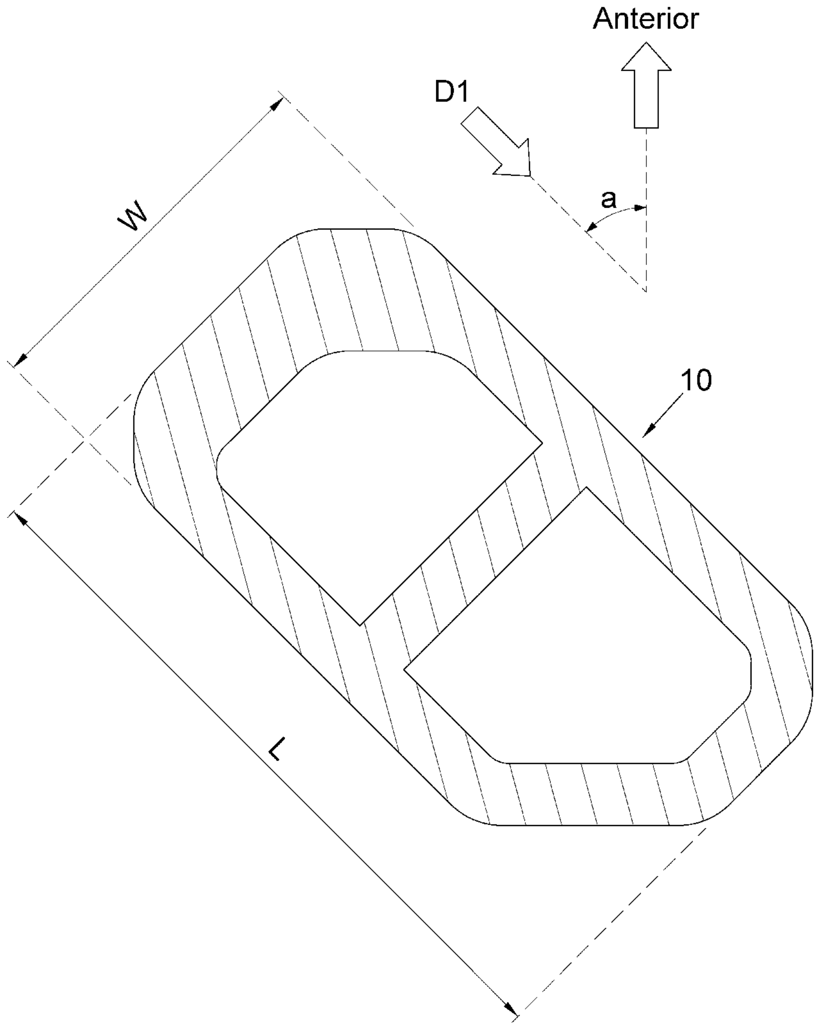
FIG. 4 is a plan view illustrating the width and length of the cage according to an embodiment of the present invention.

FIG. 4 is a plan view illustrating a width W and a length L of the cage 10 according to an embodiment of the present invention.

The width W and the length L of the cage 10 will be described on the basis of the insertion direction D1. The width W is a width that is perpendicular to the insertion direction D1. Also, the length L is a length in the insertion direction D1.

The width W and the length L of the cage 10 may vary according to the shape of the vertebral body space S and the insertion direction D1 that depends on the insertion angle a, but in the present embodiment, description will be given on the basis of the case where the width W is formed to be less than the length L. In the case where the width W is formed to be less than the length L, there is an advantage in that insertion of the cage 10 is possible even when a path for the insertion is narrow.

Figure 5:
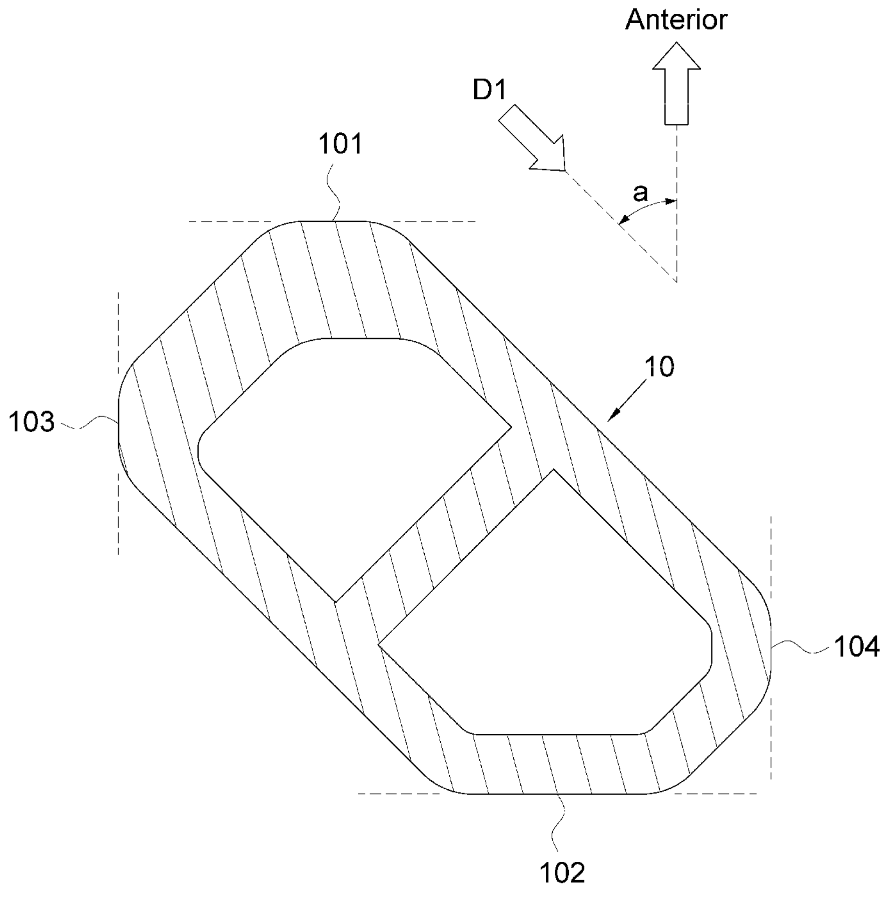
FIG. 5 is a plan view illustrating an outer peripheral surface of the cage according to an embodiment of the present invention.

FIG. 5 is a plan view illustrating the outer peripheral surface 100 of the cage 10 according to an embodiment of the present invention. When the cage 10 according to the present invention is correctly placed, the outer peripheral surface 100 corresponds to the vertebral body space S. As a preferred embodiment, the cage 10 is placed so that a front surface 101, a rear surface 102, a left surface 103, and a right surface 104 are disposed inside the vertebral body space S. In FIG. 5, dotted lines tangent to the outer peripheral surface 100 of the cage 10 show extensions of the front surface, rear surface, left surface, and right surface.

That is, the cage 10 has a shape in which, as compared to a rectangle having the width W and the length L, corners that correspond to the front surface 101, the rear surface 102, the left surface 103, and the right surface 105 are cut. The corners being cut in this way is referred to as chamfering of the corners.

Also, because the cage 10 should be inserted into the human body, in a case where the outer peripheral surface 100 includes sharp corners, the cage 10 may cause damage to muscles and nerves. Thus, preferably, the outer peripheral surface 100 may be treated to be round without any sharp corners.

Figure 6:
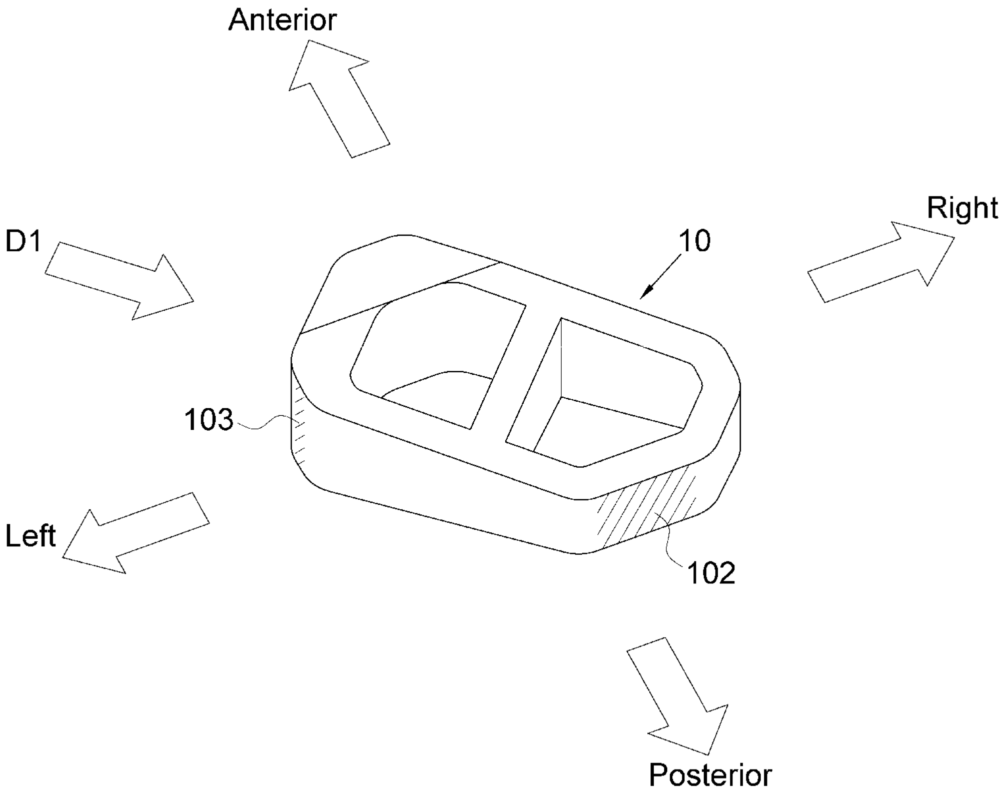
FIG. 6 is a perspective view illustrating the outer peripheral surface of the cage according to an embodiment of the present invention.

FIG. 6 is a perspective view illustrating the outer peripheral surface 100 of the cage 10 according to an embodiment of the present invention. FIG. 6 is a perspective view from an angle which is the same as the angle of FIG. 3. In FIG. 6, the rear surface 102 and the left surface 103 are indicated with hatching lines.

Figure 7:
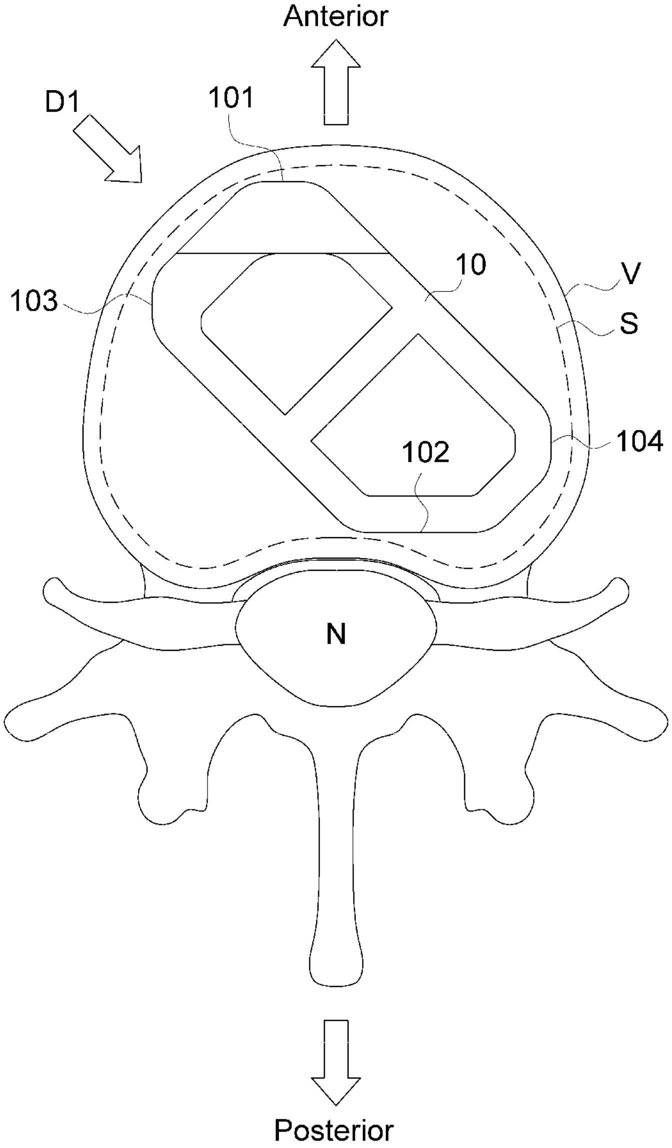
FIG. 7 is a plan view illustrating a state in which the cage is inserted between vertebrae according to an embodiment of the present invention.

FIG. 7 is a plan view illustrating a state in which the cage 10 is inserted between vertebrae according to an embodiment of the present invention. Specifically, the cage 10 is provided so that, when inserted in the insertion direction D1, the front surface 101, the rear surface 102, the left surface 103, and the right surface 104 are disposed inside the vertebral body space S. The outer peripheral surface 100 of the cage 10 corresponds to the vertebral body space S. Therefore, the cage 10 is prevented from interfering with organs around the spine and causing damage to the organs and prevented from stimulating and causing damage to nerves located behind the cage 10.

Figure 8:
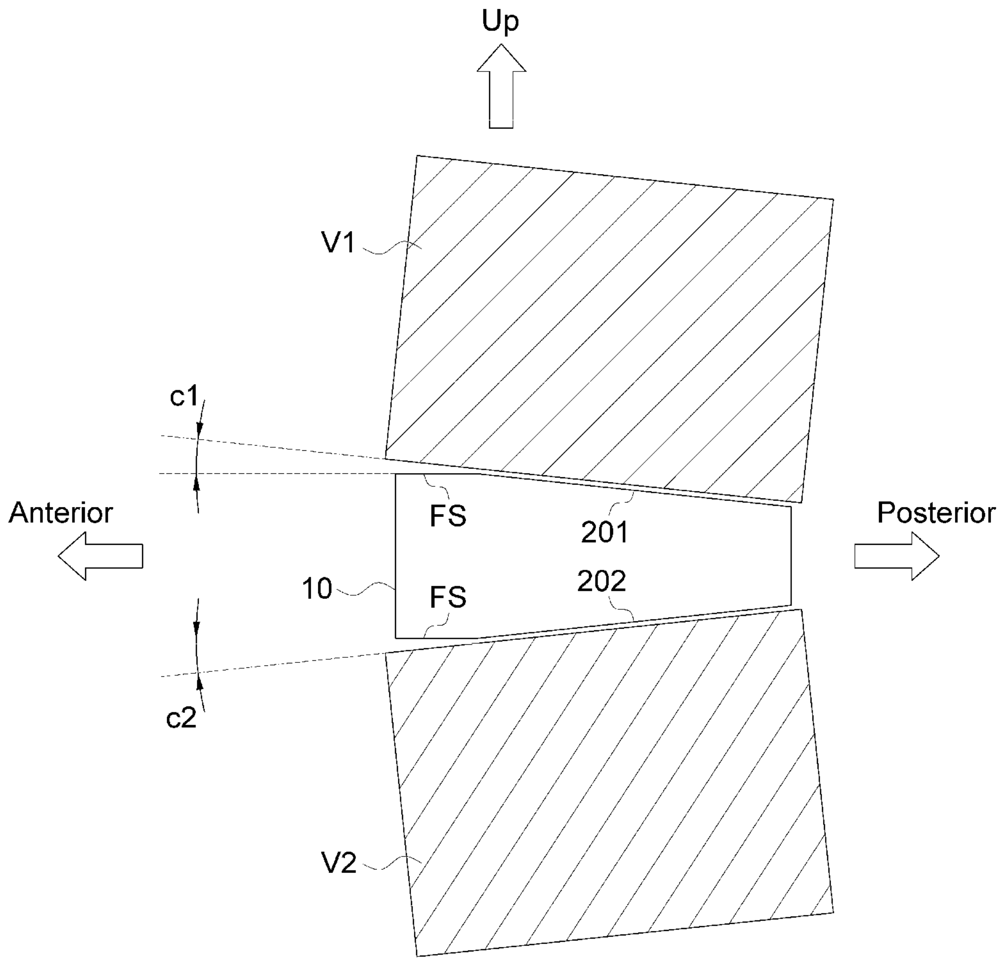
FIG. 8 is a lateral view illustrating the state in which the cage is inserted between the vertebrae according to an embodiment of the present invention.

FIG. 8 is a lateral view illustrating the state in which the cage 10 is inserted between the vertebrae according to an embodiment of the present invention. The upper bone V1 and the lower bone V2 form a predetermined angle with respect to the horizontal line along lordosis of the spine in a normal state. Hereinafter, an angle that the upper bone forms with respect to the horizontal line will be referred to as an upper angle c1, and an angle that the lower bone forms with respect to the horizontal line will be referred to as a lower angle c2.

According to the present invention, an upper inclined surface 201 and a lower inclined surface 202 are disposed at the upper surface and lower surface of the cage 10, and each inclined surface is disposed to be correctly placed when the cage 10 is inserted in the insertion direction D1. Specifically, the upper inclined surface 201 corresponds to the lower surface of the upper bone V1 when the cage 10 is correctly placed, and the lower inclined surface 202 corresponds to the upper surface of the lower bone V2 when the cage 10 is correctly placed. That is, the upper inclined surface 201 of the cage is provided as an inclined surface that forms the upper angle c1 with respect to the horizontal line, and the lower inclined surface 202 of the cage is provided as an inclined surface that forms the lower angle c2 with respect to the horizontal line.

Figure 9:
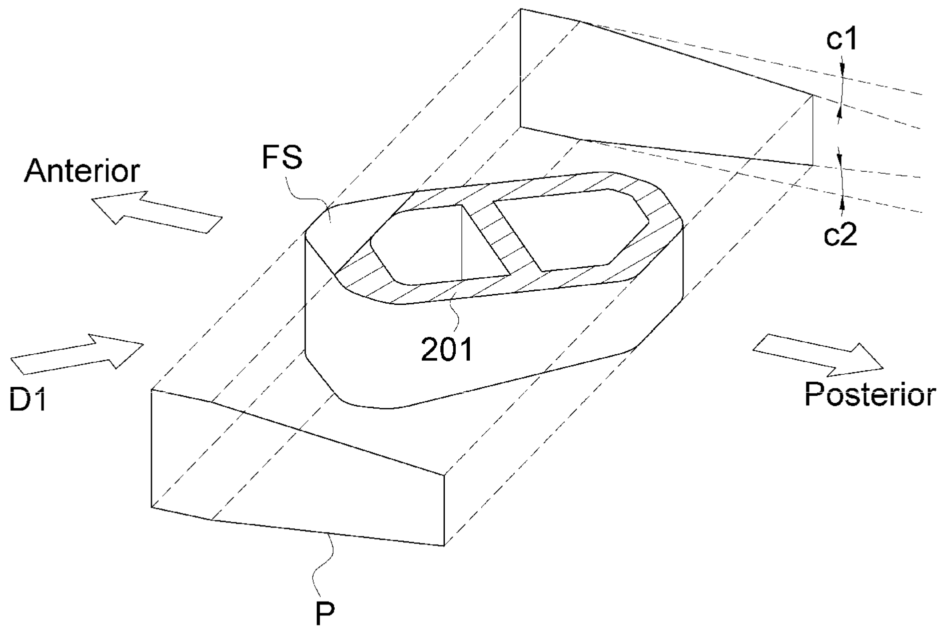
FIG. 9 is a perspective view illustrating an inclined surface of the cage according to an embodiment of the present invention.

FIG. 9 is a perspective view illustrating the inclined surface 200 of the cage 10 according to an embodiment of the present invention.

In FIG. 9, a figure P shown in an upper right direction and a lower left direction from the cage 10 shows an outline of the cage 10 projected in each lateral direction. As illustrated in FIG. 9, the upper inclined surface 201 is provided with a slope that corresponds to the upper angle c1 that the lower surface of the upper bone V1 forms with respect to the horizontal line. Although not illustrated in FIG. 9, like the upper inclined surface 201, the lower inclined surface 202 is provided with a slope that corresponds to the lower angle c2 that the upper surface of the lower bone V2 forms with respect to the horizontal line. Therefore, the cage 10 may be correctly placed when inserted in the insertion direction D1.

Meanwhile, the inclined surface 200 may be formed only in a region excluding a predetermined region FS of the anterior aspect of the vertebrae V. Therefore, a portion that corresponds to the predetermined region FS is horizontally provided and distributes a load applied to the anterior aspect of the vertebrae V. Preferably, a boundary corner of the predetermined region FS and the inclined surface 200 may be treated to be round to smoothly correspond to the vertebrae V, and thus the upper bone V1 and the lower bone V2 may not be damaged.

As described above, when inserted in the insertion direction D1, the cage 10 is correctly placed due to the outer peripheral surface 100 and the inclined surface 200 corresponding to the vertebral body space S, the upper angle c1, and the lower angle c2. Therefore, different from the conventional case where a cage is inserted through the anterior or posterior aspect, the cage 10 according to the present invention may be inserted through the oblique lateral aspect, and thus there is an effect of facilitating the insertion surgery.

Figure 10:
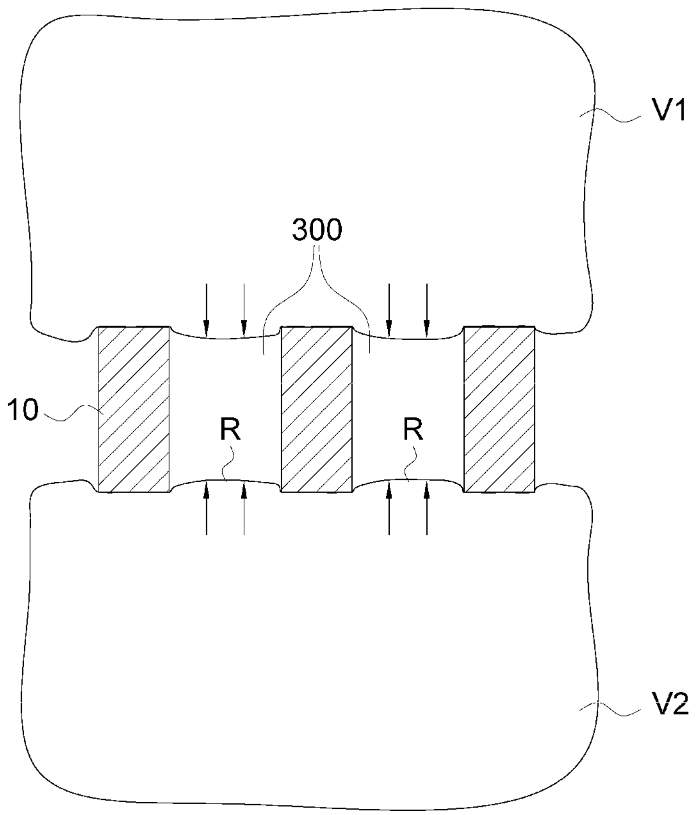
FIG. 10 is a vertical cross-sectional view illustrating a growth space of the cage according to an embodiment of the present invention.

FIG. 10 is a vertical cross-sectional view illustrating a growth space 300 of the cage 10 according to an embodiment of the present invention. The cage 10 according to the present invention may have the growth space 300 formed therein so that vertebrae that grow (R) penetrate into the growth space 300 and are fixed therein. Specifically, the growth space 300 is a space formed due to the upper surface and lower surface of the cage 10 being formed intaglio, and the upper bone V1 and the lower bone V2 in contact with the cage 10 grow and penetrate into the growth space 300. Also, the growth space 300 may be formed due to the upper surface and lower surface of the cage 10 being open to be penetrated. In the present embodiment, description will be given on the basis of the case where the growth space 300 is formed due to the upper surface and lower surface of the cage 10 being open to be penetrated.

The upper bone V1 and the lower bone V2 are supported by the cage 10, and portions of the upper bone V1 and the lower bone V2 that correspond to the growth space 300 grow (R) to penetrate into the cage 10 through the growth space 300. That is, as compared to portions of the upper bone V1 and the lower bone V2 that are supported by the cage 10, the portions of the upper bone V1 and the lower bone V2 that correspond to the growth space 300 grow (R) through the growth space 300 so that the upper bone V1 and the lower bone V2 are fused. Therefore, there is an effect of allowing the upper bone V1, the lower bone V2, and the cage 10 to be firmly coupled. Also, since the growth space 300 is provided to pass through the upper surface and lower surface of the cage 10, the load applied to the cage 10 is distributed along the periphery of the growth space 300, and thus there is an effect of stably supporting the upper bone V1 and the lower bone V2.

Figure 11:
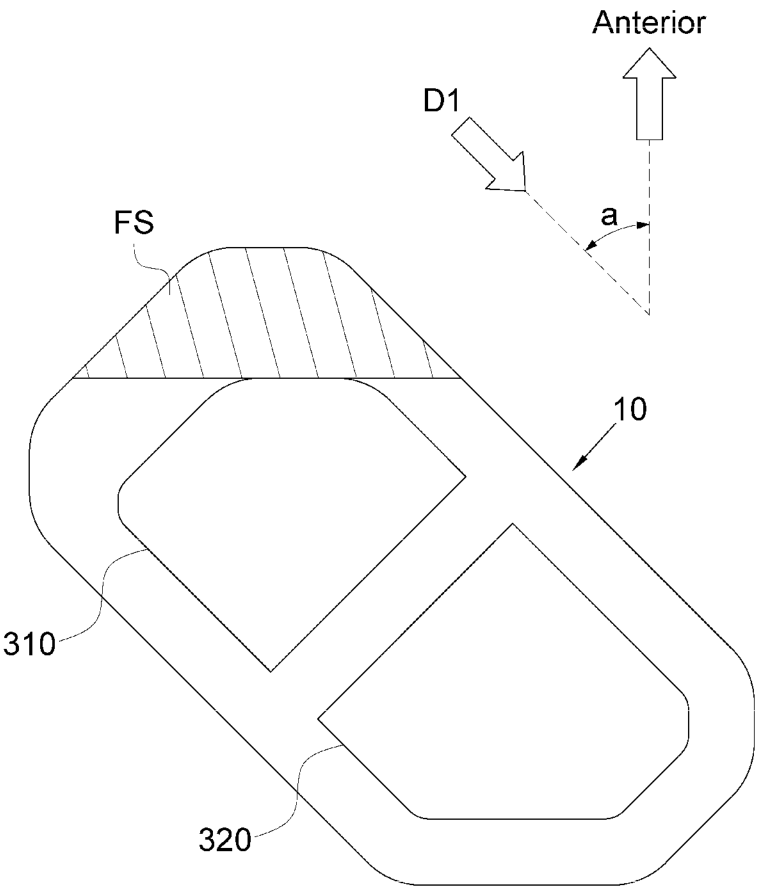
FIG. 11 is a view illustrating a position at which the growth space of the cage is formed according to an embodiment of the present invention.

Meanwhile, the load applied to the cage 10 is generally higher at the front as compared to the rear. Therefore, the growth space 300 of the cage 10 according to the present invention may be formed only at a site that corresponds to the inclined surface 200, and the growth space 300 may not be formed in the predetermined region FS. FIG. 11 is a view illustrating a position at which the growth space 300 of the cage 10 is formed according to an embodiment of the present invention. As illustrated in FIG. 11, the predetermined region FS may be provided to be completely filled without the growth space 300 formed therein and thus may distribute the load applied to the front of the cage 10.

Also, as illustrated in FIG. 11, the growth space 300 may be provided to be divided into a plurality of pieces to increase the strength of the cage 10. FIG. 11 illustrates a case where the growth space 300 is divided into a front growth space 310 and a rear growth space 320. Since each of the front growth space 310 and the rear growth space 320 distributes the load, the strength of the cage 10 is increased as compared to when a single growth space 300 is formed.

Meanwhile, in the process of inserting the cage 10, it may be difficult for an operator to identify whether the cage 10 is correctly placed just by directly observing the cage 10 with the naked eye. In order to address this, the cage 10 according to the present invention may further include a position detector 400. Specifically, one or more position detectors 400 may be disposed at predesignated positions inside the cage 10, and by being sensed through a position reading device, the position detector 400 may provide the operator with information on a precise insertion position. For example, in a case where a position reading device using a fluoroscopy means such as x-rays is disposed, the position detector 400 may be made of a metal material, and thus the position of the position detector 400 may be accurately shown by x-rays, and accordingly, the position of the cage 10 may be accurately identified.

Figure 12:
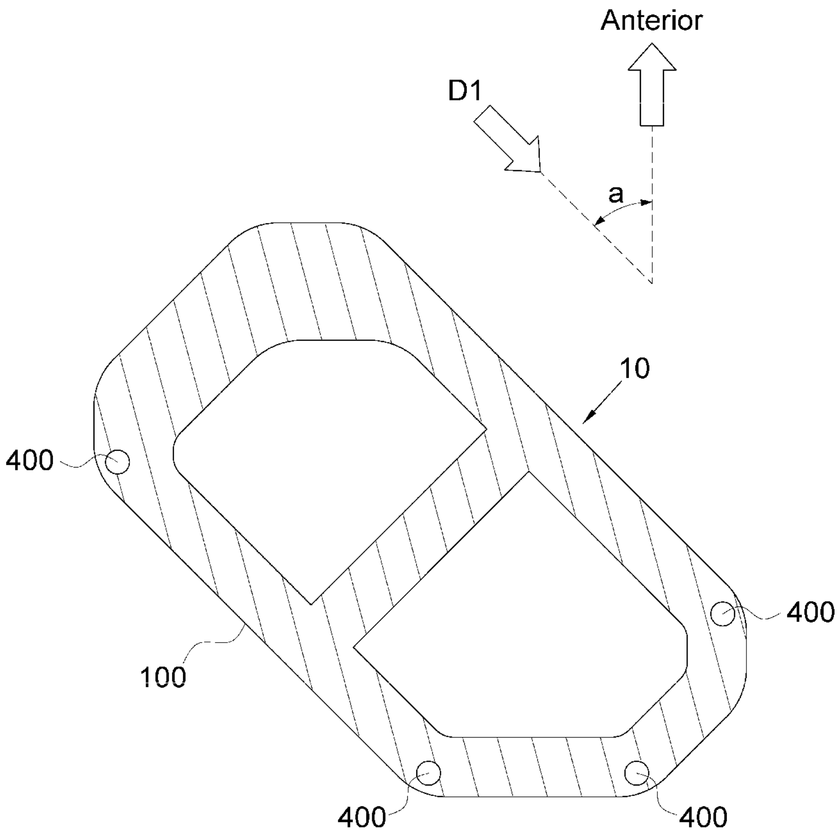
FIG. 12 is a plan view illustrating a position detector according to an embodiment of the present invention.
Figure 13:
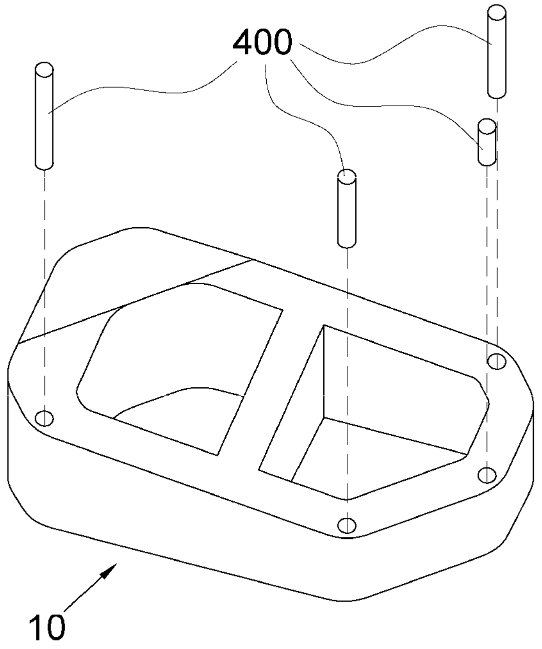
FIG. 13 is a perspective view illustrating the position detector according to an embodiment of the present invention.

FIG. 12 is a plan view illustrating the position detector 400 according to an embodiment of the present invention, and FIG. 13 is a perspective view illustrating the position detector 400 according to an embodiment of the present invention. According to the present embodiment, the position detector 400 may be provided in the form of a column that is formed in a direction toward the upper side and lower side of the cage 10. Also, each position detector 400 may be provided to be disposed along an edge of the cage 10. Due to the position detector 400 being disposed along the edge of the cage 10, even when the outer peripheral surface 100 of the cage 10 is not directly shown on the position reading device, the outer peripheral surface 100 of the cage 10 may be identified by the position detector 400.

Also, the position detector 400 according to the present invention may be provided in the form of a column and may be provided to pass through the upper surface and lower surface of the cage 10.

Figure 14:
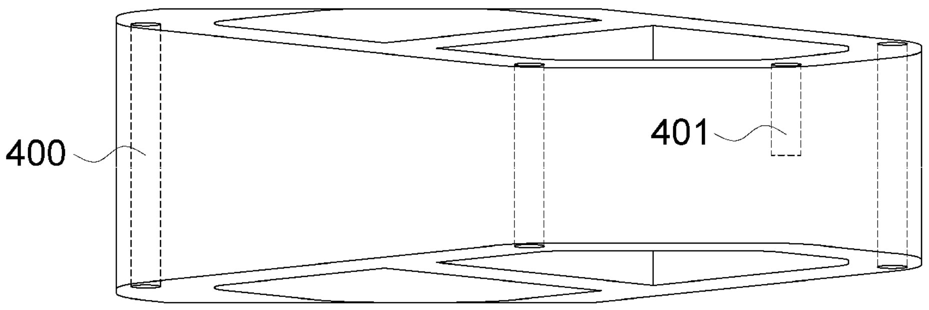
FIG. 14 is a rear view illustrating the position detector according to an embodiment of the present invention.

FIG. 14 is a rear view illustrating the position detector 400 according to an embodiment of the present invention. Since each position detector 400 is provided to pass through the upper surface and lower surface of the cage 10, even when the upper surface and lower surface of the cage 10 are not directly shown on the position reading device, the upper surface and lower surface of the cage 10 may be identified by the position detector 400.

Also, in the case where the cage 10 is not directly shown on the position reading device, it may be difficult to distinguish the top and bottom of the cage 10. In order to address this, one or more top/bottom detectors 401 may be disposed. Specifically, the position detector 400 is provided with a length that allows the position detector 400 to pass through the upper surface and lower surface of the cage 10, and the top/bottom detector 401 is provided with a length shorter than the length of the position detector 400 and is provided to only pass through either one of the upper surface and lower surface of the cage 10. Therefore, due to the top/bottom detector 401, the top and bottom of the cage 10 are asymmetrically shown, and through the asymmetry of the position detector 400 shown on the position reading device, the top and bottom of the cage 10 may be distinguished. In the present embodiment, description has been given on the basis of the case where the top/bottom detector 401 only passes through the upper surface of the cage 10.

Figure 15:
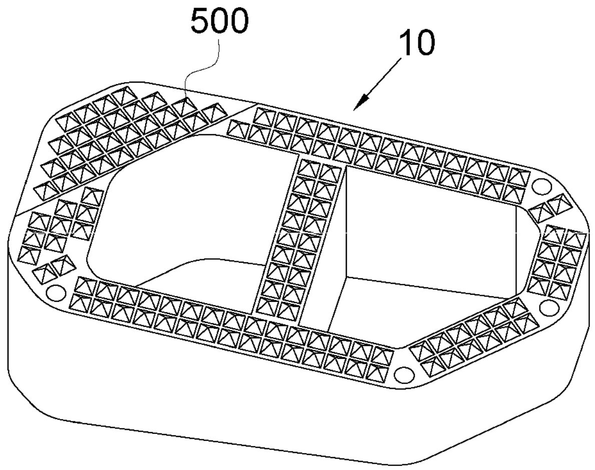
FIG. 15 is a perspective view illustrating a protrusion according to an embodiment of the present invention.

Meanwhile, the cage 10 according to the present invention may further include a plurality of protrusions 500 disposed on the upper surface and lower surface thereof. FIG. 15 is a perspective view illustrating the protrusions 500 according to an embodiment of the present invention. Due to the plurality of protrusions 500 formed to protrude from the upper surface and lower surface of the cage 10, the cage 10 may be firmly coupled to the upper bone V1 and the lower bone V2. Due to being fixed between the upper bone V1 and the lower bone V2 by the protrusions 500 in addition to being fixed through the growth space 300, the cage 10 may be prevented from being detached and may stably support the upper bone V1 and the lower bone V2.

In order to insert the cage 10 according to the present invention between vertebrae, an insertion tool 610 in the shape of a long bar may be used to facilitate an approach of the cage 10 toward the inside of the human body. Also, for the cage 10 to be precisely inserted at an insertion position, the cage 10 should be firmly fastened to the insertion tool 610. To this end, the cage 10 according to the present invention may include an insertion tool fastening portion 600.

Figure 16:
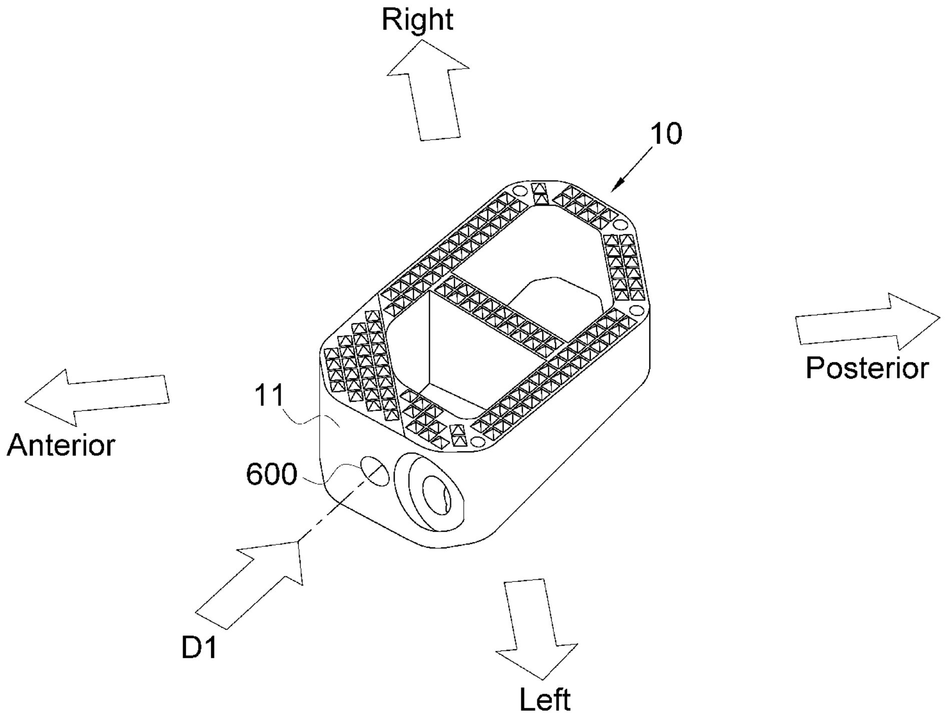
FIG. 16 is a perspective view illustrating an insertion tool fastening portion according to an embodiment of the present invention.
Figure 17:
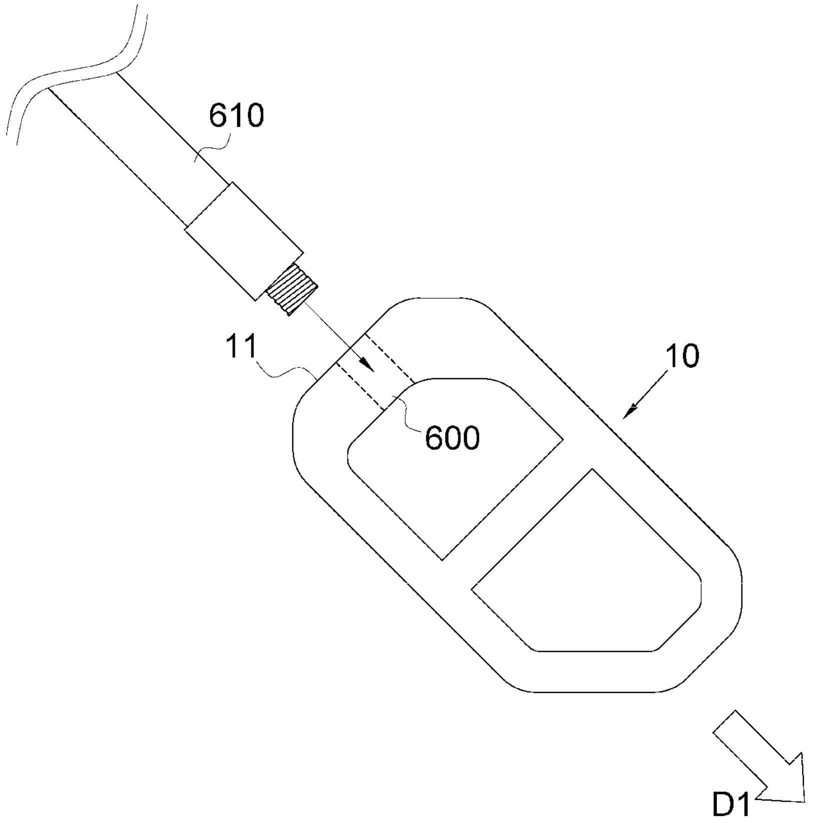
FIG. 17 is a plan view illustrating the insertion tool fastening portion according to an embodiment of the present invention.

FIG. 16 is a perspective view illustrating the insertion tool fastening portion 600 according to an embodiment of the present invention, and FIG. 17 is a plan view illustrating the insertion tool fastening portion 600 according to an embodiment of the present invention. Hereinafter, a surface of the cage 10 that is in a direction opposite to the insertion direction D1 will be referred to as an "operation surface." Due to the insertion tool fastening portion 600 being disposed on the operation surface 11, the insertion tool 610 may be easily unfastened and removed after the cage 10 is inserted. As a preferred embodiment, the insertion tool fastening portion 600 may be provided in a screw-coupling manner, and the insertion tool 610 may have one end provided in the form of a screw. Due to the insertion tool fastening portion 600 being provided in a screw-coupling manner, the cage 10 may be firmly fastened to the insertion tool 610 during the insertion surgery, and fastening and unfastening of the insertion tool 610 are facilitated. Also, after the insertion tool 610 is unfastened, the insertion tool fastening portion 600 does not protrude past the outer peripheral surface 100 of the cage 10.

Figure 18:
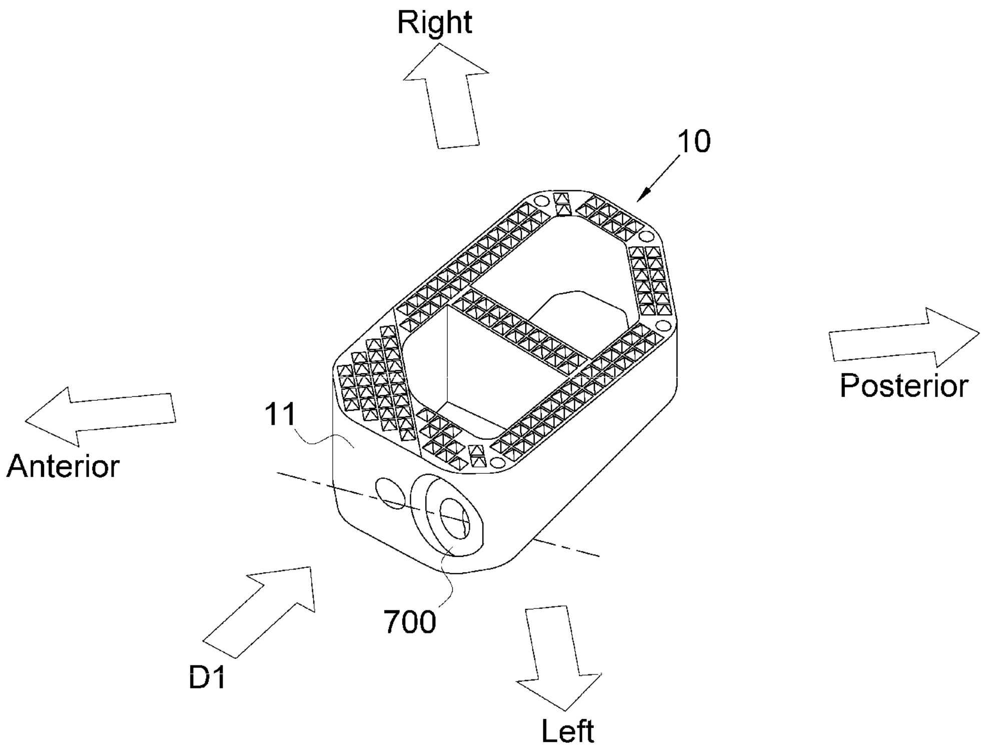
FIG. 18 is a perspective view illustrating a screw hole according to an embodiment of the present invention.
Figure 19:
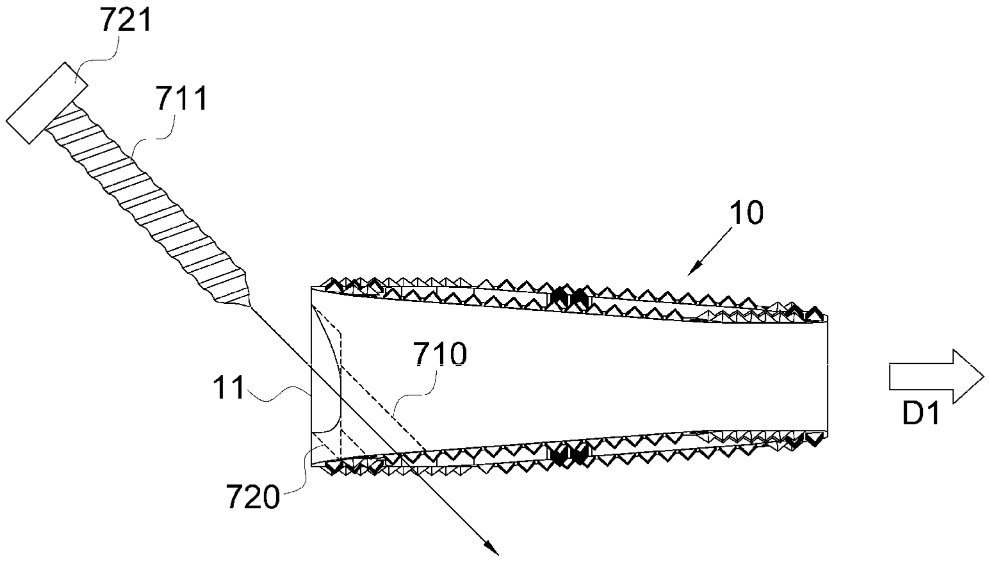
FIG. 19 is a rear view illustrating the screw hole according to an embodiment of the present invention.

Also, the cage 10 according to the present invention may further include a screw hole 700 to be firmly coupled to the upper bone V1 or the lower bone V2. FIG. 18 is a perspective view illustrating the screw hole 700 according to an embodiment of the present invention, and FIG. 19 is a rear view illustrating the screw hole 700 according to an embodiment of the present invention. Specifically, the screw hole 700 may be provided to pass through the operation surface 11 of the cage 10 and the upper surface or lower surface of the cage 10. In the present embodiment, description will be given on the basis of the case where the screw hole 700 passes through the lower surface of the cage 10. Due to the screw hole 700 being provided, the cage 10 may be firmly fixed to the lower bone V2 using a coupling screw. Also, due to the screw hole 700 being provided on the operation surface 11 which is in the direction opposite to the insertion direction, the coupling screw may be easily inserted in the surgical process.

Also, the screw hole 700 may include a screw head storage 720. The screw head storage 720 may be provided on the operation surface 11 and formed intaglio with a diameter larger than a diameter of a path 710 through which the screw passes. In this way, a head 721 of the coupling screw may be prevented from protruding past the outer peripheral surface of the cage.

As described above, through the present invention, it is possible to provide the cage 10 that is able to be inserted through the oblique lateral aspect and thus reduces the risk of damage to organs, muscles, and nerves around the spine. Also, since it is possible to easily identify the insertion position of the cage 10, side effects due to erroneous insertion of the cage 10 may be prevented, and the cage 10 may be firmly fixed and stably support the vertebrae. In addition, since the process of insertion surgery is simple and the surgery time is reduced, a burden on the patient may be reduced.

The preferred embodiments of the present invention described above have been disclosed only for illustrative purposes. Those of ordinary skill in the art to which the present invention pertains may make various modifications, changes, and additions within the spirit and scope of the present invention, and such modifications, changes, and additions should be construed as belonging to the scope of the attached claims.

Since those of ordinary skill in the art to which the present invention pertains may make various substitutions, alterations, and changes within the scope not departing from the technical spirit of the present invention, the present invention is not limited by the embodiments described above and the accompanying drawings.

[Description of reference numerals]

| | |
|---|---|
| 10: cage | |
| 100: outer peripheral surface | 200: inclined surface |
| 201: upper inclined surface | 202: lower inclined surface |
| 300: growth space | 400: position detector |
| 500: protrusion | 600: insertion tool fastening portion |
| 700: screw hole | |
| D1: insertion direction | a: insertion angle |
| N: nerve | S: vertebral body space |
| V: vertebra | |

INDUSTRIAL AVAILABILITY

According to the present invention, a risk of damage to organs, muscles, and nerves is reduced in the process of cage insertion surgery.

Also, according to the present invention, the process of cage insertion surgery is facilitated.

Also, according to the present invention, the cage can be stably fixed, and thus side effects after surgery can be reduced.

Also, according to the present invention, the surgery time is reduced, and thus a burden on the patient is reduced.

In addition, according to the present invention, advantages of anterior insertion and posterior insertion are combined, and thus post-surgery outcomes in patients can be improved.

The invention claimed is:

1. A cage configured to be inserted between a plurality of vertebrae, the cage comprising planar inclined surfaces including an upper planar inclined surface and a lower planar inclined surface, wherein the cage is configured to be supported while being inserted in an insertion direction to form an insertion angle with respect to an anterior aspect of the spine and being configured to be placed between the plurality of vertebrae, wherein the upper and lower planar inclined surfaces are disposed from an anterior aspect to a posterior aspect of the plurality of vertebrae such that, when placed between the plurality of vertebrae, the upper planar inclined surface forms an upper angle with respect to an upper planar horizontal surface, and the lower planar inclined surface forms a lower angle with respect to a lower planar horizontal surface, wherein the cage further comprises the upper planar horizontal surface connected to the upper planar inclined surface and disposed on an upper end portion of the cage, and the lower planar horizontal surface connected to the lower planar inclined surface and disposed on a lower end portion of the cage, the upper and lower end portions of the cage being configured to be placed adjacent to the anterior aspect of one of the plurality of vertebrae, respectively, wherein the upper and lower planar horizontal surfaces are horizontally provided and configured to distribute a load applied to the anterior aspect of the plurality of vertebrae, and wherein, in the cage:

an open growth space is formed in the upper and lower planar inclined surfaces for growth of the plurality of vertebrae; and the upper and lower planar horizontal surfaces are provided to be completely filled to support the plurality of vertebrae.

2. The cage of claim 1, wherein, a width of the cage is perpendicular to the insertion direction and is disposed to be less than a length of the cage in the insertion direction in which the cage is inserted.

3. The cage of claim 1, wherein the open growth space is configured such that the plurality of vertebrae are able to grow and penetrate into the open growth space and be fixed therein.

4. The cage of claim 1, wherein the open growth space is defined by one or more openings disposed on the upper and lower planar inclined surfaces, and the open growth space provides a space in which an upper bone and a lower bone grow and fuse.

5. The cage of claim 1, wherein one or more position detectors configured to detect whether the cage is placed are disposed at positions inside the cage.

6. The cage of claim 5, wherein the one or more position detectors are disposed along an edge of the cage.

7. The cage of claim 5, wherein:

the one or more position detectors are provided with a length that allows the one or more position detectors to pass through the upper and lower planar inclined or horizontal surfaces of the cage;

at least one of the one or more position detectors is a top/bottom detector;

the top/bottom detector is provided with a length shorter than a length of another one of the one or more position detectors; and the top/bottom detector is provided to only pass through one of the upper planar inclined surface and the upper planar horizontal surface, or one of the lower planar inclined surface and the lower planar horizontal surface.

8. The cage of claim 1, wherein an insertion tool fastening portion is disposed on an operation surface of the cage in a direction opposite to the insertion direction of the cage.

9. The cage of claim 1, wherein a screw hole is disposed to pass through an operation surface of the cage, which is in a direction opposite to the insertion direction of the cage, and one of the lower planar inclined surface and the lower planar horizontal surface of the cage to fix the cage to the plurality of vertebrae.

* * * * *